United States Patent [19]

Caspe

[11] 4,308,257
[45] Dec. 29, 1981

[54] ACCELERATING CELLULAR REPAIR COMPOSITION FOR THE HUMAN BODY AND METHOD OF ADMINISTERING SAME

[76] Inventor: Saul Caspe, 54 W. 16th St., New York, N.Y. 10011

[21] Appl. No.: 156,190

[22] Filed: Jun. 3, 1980

[51] Int. Cl.³ .................... A61K 31/44; A61K 31/465
[52] U.S. Cl. ..................................... 424/180; 424/177
[58] Field of Search ............................... 424/180, 177

[56] References Cited

PUBLICATIONS

Straub, *Biochem. J.*, vol. 33, pp. 787 et seq. (1939).
Caspe, *J. Cell and Comp. Physiol.*, vol. 27, No. 1, pp. 43–52, (1946).
Green, *J. Biol. Chem.*, vol. 135, p. 345 (1940).

*Primary Examiner*—John M. Ford
*Attorney, Agent, or Firm*—A. W. Breiner

[57] ABSTRACT

The present invention comprises a composition of matter and method for introducing the composition of matter into the human body to achieve cellular repair. The composition comprises as a first component a stable, pyrogen-free liquid mixture containing an amino acid metabolite, a thiamine salt, diphosphopyridine nucleotide, diaphorase flavin protein enzyme, and a carrier in select ratios, and as a second component an enteric coated tablet comprising nicotineamide, adenosine-5-monophosphate, diphosphopyridine nucleotide, and an inert carrier in select ratios. The first component is administered by subcutaneous injection, followed by ingestion of the second component. This invention is particularly useful in healing ulcers, burns, post-operative wounds, and various skin disruptions of diabetics.

3 Claims, No Drawings

ACCELERATING CELLULAR REPAIR COMPOSITION FOR THE HUMAN BODY AND METHOD OF ADMINISTERING SAME

It has been found that certain enzyme components of the human body decrease in the body under various conditions, such as advanced age, internal ulcerations, shock, severe burns, and various metabolic diseases.

Specifically, respiratory enzymes such as diaphorase, diphosphopyridine nucleotide (coenzyme-1), and creatine are critical to the respiration mechanisms of cells. These enzymes have been found essential in the oxidation of the amino acids and the carbohydrates in cells. The resultant glycolysis and amino acid oxidation translates in vivo to cell proliferation.

In 1913 Carrel showed that muscle and gland tissue extracts stimulated the growth rate of homologous fibroblasts in vitro. Diaphorase was isolated by Straub in 1939, *Biochem J.,* 33:787 (1939). Caspe described the stimulating effect upon cell proliferation including human fibroblasts and that the addition of coenzymes and creatine produced a synergistic effect, *J. Cell and Comp. Physiol.,* V. 27, No. 1, pp. 43–52 (1946). Caspe in a series of reports established the reduction of coenzyme-1 in the blood of patients with ulcerative colitis and duodenal ulcers, that creatine levels were reduced in diabetes and muscular degeneration and that creatine was necessary for cell growth in chick, mouse, rat, and human tissue in tissue cultures, *Clinical Chemistry,* Vol. 4, No. 5, pp. 374–78 (1958); *Amer. J. of Physiol.,* V. 159, No. 3, pp. 461–66 (1949).

It has now been discovered that abnormal metabolic conditions can be improved when the stable, pyrogen-free liquid mixture described below is periodically introduced into the body subcutaneously, followed by the periodic introduction into the body by ingestion of a tablet described in detail below. This two-part treatment has been found effective in stepping up various regenerative processes and healing in conditions such as peptic and duodenal ulcers, external ulcers, skin grafting, burns, and post-operative wounds. Of particular significance is the healing of diabetic wounds and skin ulcers which are generally recognized as slow healing. These results are listed in Tables 1 and 2 below.

Part 1 of the treatment method is the induction of initial healing by the subcutaneous injection of a stable, pyrogen-free liquid mixture comprising:

from 0.025 to 0.075% by wt. arginine or creatine (amino acid metabolite);
from 0.1 to 0.2% by wt. of a thiamine salt;
from 0.06 to 0.11% by wt. of coenzyme-1;
from 0.0001 to 0.0003% by wt. of diaphorase flavin protein enzyme;
with the balance an inert carrier,
wherein the weight ratios of—
  (a) amino acid metabolite to thiamine salt is from between about 0.05:0.15 and about 0.075:0.2, and
  (b) codehydrogenase (coenzyme-1) to diaphorase flavin protein enzyme is from between about 0.06:0.0001 and about 0.11:0.0003, and
the concentration of diaphorase flavin protein enzyme per ml. of tissue substrate is from between about 0.78 ug. and about 0.39 ug.

Part 2 of the treatment is the maintenance of the healing induced in Part 1 and comprises the subsequent periodic ingestion of tablets comprising nicotineamide, adenosine-5-monophosphate, codehydrogenase (coenzyme-1), and inert carrier, wherein the tablet is enteric coated with up to 20 coats of cellulose acetate phthalate. The two steps are repeated at various frequencies as described below. Specific examples of the two-step process are described in Tables 1 and 2 below.

The diaphorase used in the present invention is made according to the method of Straub, *Biochem J.,* 33:787 (1939). The diphosphopyridine nucleotide (codehydrogenase) used in the invention is made according to the method of D. E. Green, *J. Biol. Chem.,* 135:345 (1940).

To control various abnormal metabolic conditions and to stimulate recovery towards normal metabolic conditions, it has been observed that the concentration of certain proliferative elements must be routinely supplemented. Certain supplements are required at two levels, one mixture at a "peak level" obtained by periodic subcutaneous injection at a concentration of from about 0.5 to about 1.0 ml. at a frequency of from once every 24 hours to once every 96 hours; and the second mixture at a "minimal level" obtained by the oral ingestion of an enteric coated tablet having a composition and concentration different from the injectible. It is critical to the combined effect of the "peak" and "minimal" compositions that the latter pass to the intestine before the active agents are absorbed by the body. That is, the active agents must pass through the stomach encapsulated and enter the intestine intact in order to avoid the deactivating that would occur in the stomach.

Two specific examples of the injectible compositions of the invention and which are a stable, pyrogen-free mixture are as follows:

I.

50 mg. creatine
90 mg. DPN.4 $H_2O$ (diphosphopyridine nucleotide)
150 mg. thiamin Hcl
0.1 mg. diaphorase flavin protein enzyme; and

II.

75 mg. creatine
108 mg. DPN.4 $H_2O$
200 mg. thiamin Hcl
0.2 mg. diaphorase flavin protein enzyme.

The concentrations of the above-stated components were added to 100 ml. of aqueous physiological saline (850 mg. Nacl) containing 300 mg. of phenol. This liquid medium was tested and found to be pyrogen free. To this solution was added 0.05 mg./ml. of riboflavin-5-phosphate which adds color to the solution and acts as an indicator. The solution is now ready for vialing to be used for subcutaneous injection when the proper dose is withdrawn into the chamber of the injection unit. The preparation is now ready for clinical testing.

An oral capsule suitable for the invention was prepared containing:

Coenzyme-1: 0.001 gm./per cap.
Nicotineamide: 0.1 gm./per cap.
Adenylic Acid (adenosine-5-mono phosphate): 0.025 gm./per cap.
Diluent: lactose 0.124 gm./per cap.
Indicator: riboflavin 0.0001 gm./per cap., and then was enteric coated with up to 20 coats cellulose acetate phthalate.

TABLE 1

| Example | Abnormal Metabolic Condition Treated | Frequency Of Injection/Amount | Results |
|---|---|---|---|
| 1 | Chronic erosion of cervix, metaplasia of tubes and ovaries, hyperplastic endometrium and $CM^2$ circular ulcer on the right vaginal vault. | 0.5 ml. 3 × a week | Ulcer healed in 6 weeks and remained healed a year later when last examined. |
| 2 | Diabetic with post amputation of gangrenous toe wound - also wound on middle toe. | 0.5 ml. 3 × a week | Middle toe wound healed within 2-3 weeks. Post-operative gangrenous toe wound completely healed within 3 months. |
| 3 | Diabetic, mature diabetic knee cap injured in fall - several pustules appeared. | 0.5 ml. 3 × a week | All healed within 2 weeks. |
| 4 | Recurring sore from crushed leg injury and ensuing phlebitis - given injection of cicatrase and penicillin. | 0.5 ml. 3 × a week | Healed in 2 weeks. |
| 5 | Duodenal ulcer recurring for several years. | 0.5 ml. 3 × a week | Healed in 2 weeks. |
| 6 | Duodenal ulcer of recent origin. | 0.5 ml. 3 × a week | Healed in 2 weeks - confirmed by X-ray. |
| 7 | Duodenal ulcer/chronic gastritis. | 1.0 ml. 2 × a week, followed by 0.5 ml. 3 × a week | Completely healed in 2 weeks - no recurrence of symptoms. |
| 8 | Ulcers on dorsun of left foot; 3 years previously a 10,000 volt electric line had fallen on foot inflicting severe burns, ulcers - continued after skin grafting broke down. | 1.0 ml. 3 × a week | Foot healed in 3 weeks. |
| 9 | Buergers disease with high-grade arterial occlusion of long-standing chronic ulcer of great toe present for over 6 months. | 0.5 ml. 3 × a week | Healed within 1 month. |
| 10 | Ulcerative colitis. | 0.5 ml. 3 × a week | Healed within 1 month. |
| 11 | Gastric ulcer patient in excruciating pain - given cicatrase after all other methods failed. Recurrence of ulcer within year. | 1.0 ml. 3 × first week 0.5 ml. 3 × second week 1.0 ml. daily | Pain subsided in 3 days - completely healed in 2 weeks - X-ray evidence. Recurrence/responded to cicatrase - healed in 1 week - X-ray evidence. |
| 12 | Ulcerative colitis - 8-14 stools daily with mucous and blood and pus and polyps. | 1.0 ml. 2 × a week | Discharged in excellent condition in 3 weeks - stools now 2 in number. |
| 13 | Ulcerative colitis - 6-8 bloody stools daily. | 0.5 ml. 3 × a week | Complete healing in 6 weeks. Protoscopy reveals normal mucous membrane. |
| 14 | Chronic ulceration of left foot in the planter surface of the great toe in peripheral arteriosclerosis. | 0.5 ml. 3 × a week | Ulcer healed within 2 weeks and remained healed for 2 years. |
| 15 | Chronic inflammatory fibrotic nodule of chin. | 1.0 ml. 3 × a week for 2 weeks and extended for additional week | After superficial X-ray therapy, 3 skin units, lesion diminished somewhat in size, but chronic inflammatory granulation continued. Operation - excision of lesion performed, followed by period of injection of cicatrase 3 weeks - complete healing with thin linear scar. |
| 16 | Various ulcers of right leg of several months duration. | 0.5 ml. 2 × a week | 3 weeks of cicatrase, 6 doses, resulted in complete healing. |
| 17 | Deformity of duodenal bulb and ulcer. | 1.0 ml. - 1 I.M. 2 × a week 6 injections total | Banthine and Sippy diet showed temp. improvement. Complete relief and healing within 3 weeks after 6 I.M. injections of cicatrase. |
| 18 | Gastric ulcer. | 1.0 ml. 3 × a week 7 injections total | Gastric ulcer healed in 2 weeks after 7 injections of cicatrase. |
| 19 | Ulcerative colitis with fissures. | 1.0 ml. 3 × a week | 14 injections cicatrase for 4 weeks resulted in excellent results in healing the condition of this patient. |

TABLE 2

| Example | Abnormal Metabolic Condition Treated | Frequency Of Injection/Amt. And Ingestion Of Tablet | Results |
|---|---|---|---|
| 20 | Mature diabetic-blood sugar in | 0.7 mg. Co-1/injected | Blood sugar reduced to 189 mg. % |

TABLE 2-continued

| Example | Abnormal Metabolic Condition Treated | Frequency Of Injection/Amt. And Ingestion Of Tablet | Results |
|---|---|---|---|
| | 200 mg. % maintained on 1600 cal. diet - urine sugar 1%. | weekly, plus 1 capsule daily | in 1 week, followed by further reduction to 150 mg. %; blood sugar and faint test in sugar urine maintained for 4 weeks; when discontinued capsules and injections of Co-1 high blood sugar returned to 240 mg. % and 1.2% urine sugar. |
| 21 | Juvenile diabetic-blood sugar 480 mg. % on 45 units insulin and 4.0% urine sugar; numerous and unhealed sores. | 0.7 mg. Co-1/injected weekly, plus 1 capsule daily | Blood sugar reduced to 175 within 1 week; within 3 weeks, B.S. reduced insulin to 30 units and B.S. continues to be reduced to 160 and 140% and urine sugar 1%. All sores completely healed. |
| 22 | Mature diabetic on 1600 cal. diet; several unhealed sores. | 1 capsule daily for 1 week | All sores completely healed at the end of a week. |
| 23 | Juvenile diabetic on 1600 cal. diet, plus 25 units insulin; blood sugar 250 mg. %; unhealed sores - a few body ulcers. | 2 capsules daily for 2 weeks | All sores and ulcers healed in 2 weeks. Also, blood sugar reduced considerably. Reduced insulin to 20 units. |
| 24 | Mature diabetic at age 69-high blood sugar and urinary sugar - associated - high blood pressure. Given 10 units NPH insulin daily, Diuril and later Roniacol 3 × a week. At age 73 taken off insulin and kept on 1600 cal. diet. At 74 years developed 2 sores which remained unhealed for several weeks. | 1 capsule daily for 4 days | Blood sugar normal and blood pressure normal. Both sores completely healed within 4 days. |
| 25 | Mature diabetic-220 mg. % blood sugar, sores developed from scratching; kept on 1600 cal. diet. | 2 capsules daily for 2 days, then 1 capsule daily for 6 days | Complete healing of sores within 9 days; slight reduction in blood sugar to 180 mg. %. |
| 26 | Mature diabetic-280 mg. % blood sugar and 2.2% urine sugar; a few non-healing sores. | 0.7 mg. Co-1 injected for 2 days, followed by 2 capsules daily for 6 days | Sores completely healed in 8 days; also, noticeable drop in blood sugar H.T. urinary sugar. |
| 27 | Juvenile diabetic-150 mg. % blood sugar plus H.T. urinary sugar; 2 skin ulcers. | 2 capsules for 3 days, and then 1 capsule for 3 days | Complete healing of ulcers in 6 days. |
| 28 | Mature diabetic with a few unhealed sores. | 1 capsule daily for 5 days | Complete healing by the 6th day. |
| 29 | Ulcer of duodenum recurrent for several years. | 3 injections of 0.5 ml. daily for 3 days, followed by 1 capsule daily for following 3 days | Remission of all symptoms after the 6-day treatment. |
| 30 | Gastric ulcer causing excrutiating painful distress. | 4 injections of 1.0 ml. daily for 4 days, followed by 1 capsule daily for following 4 days | Complete recovery after 8 days. |
| 31 | Ulcerative colitis, about 10 bloody stools daily. | 4 injections of 1.0 ml. daily for 4 days, followed by 1 capsule daily for 6 days | After 12 days, stools 2 a day, mucosa appears normal. |
| 32 | Duodenal ulcer. | 2 injections of 0.5 ml. daily for 2 days, followed by 2 capsules daily for 2 days, reduced to 1 capsule daily for 3 cays | Ulcer healed in one week. |

It is claimed:

1. A two-part system for accelerating cellular repair comprising an injectible liquid mixture formulated to produce an initial positive response to certain abnormal metabolic conditions comprising:

(A)
(a) an amino acid metabolite selected from the group consisting of arginine, creatine, and mixtures thereof in a concentration from between about 0.025% and about 0.075% by weight,
(b) a thiamine salt in a concentration from between about 0.1% and about 0.2% by weight,
(c) diphosphopyridine nucleotide in a concentration from between about 0.06% and about 0.11% by weight,
(d) diaphorase flavin protein enzyme at an activity from between about 0.0001% and about 0.0003% by weight derived from animal muscles and characterized by the presence of a protein moiety that promotes respiratory activity on cells, and
(e) the remainder an inert carrier;
wherein:

(1) the weight ratio of the amino acid metabolite to the thiamine salt is from between about 0.05:0.15 and about 0.075:0.2;

(2) the weight ratio of diphosphopyridine nucleotide to diaphorase flavin protein enzyme is from between about 0.06:0.0001 and about 0.11:0.0003, and (3) the concentration of diaphroase flavin protein enzyme per ml. of tissue substrate is from between about 0.78 ug. and about 0.39 ug.; and (B) a respiratory enzyme booster tablet which will produce a maintenance response to abnormal metabolic conditions comprising an enteric coated substance containing a mixture of diphosphopyridine nucleotide, nicotineamide, adenosine-5-monophosphate, and an inert carrier wherein the enteric coating is cellulose acetate phthalate.

2. A method of treating abnormal metabolic conditions comprising:

(A) periodically introducing subcutaneously a pyrogen-free, stabilized liquid mixture comprising:

(a) an amino acid metabolite selected from the group consisting of arginine, creatine, and mixtures thereof in a concentration from between about 0.025% and about 0.075% by weight, (b) a thiamine salt in a concentration from between about 0.1% and about 0.2% by weight, (c) diphosphopyridine nucleotide in a concentration from between about 0.06% and about 0.11% by weight, (d) diaphorase flavin protein enzyme at an activity from between about 0.0001% and about 0.0003% by weight derived from animal muscles and characterized by the presence of a protein moiety that promotes respiratory activity on cells, and (e) the remainder an inert carrier; and (B) periodically introducing by ingestion an enteric control mixture comprising diphosphopyridine nucleotide, nicotineamide, adenosine-5-monophosphate, and an inert carrier.

3. A method of treating diabetic wounds and ulcers comprising:

(A) periodically introducing subcutaneously a pyrogen-free, stabilized liquid mixture containing diphosphopyridine nucleotide, and (B) periodically introducing by ingestion a mixture comprising diphosphopyridine necleotide, nicotineamide, adenosine-5-monophosphate, and an inert carrier.

* * * * *